United States Patent [19]

Hiatt et al.

[11] Patent Number: 4,801,540
[45] Date of Patent: Jan. 31, 1989

[54] PG GENE AND ITS USE IN PLANTS

[75] Inventors: William R. Hiatt; Raymond E. Sheehy; Christine K. Shewmaker; Jean C. Kridl; Vic Knauf, all of Davis, Calif.

[73] Assignee: Calgene, Inc., Davis, Calif.

[21] Appl. No.: 201

[22] Filed: Jan. 2, 1987

Related U.S. Application Data

[63] Continuation-in-part of Ser. No. 920,574, Oct. 17, 1986, which is a continuation-in-part of Ser. No. 845,676, Mar. 28, 1986, abandoned.

[51] Int. Cl.[4] ................... C12N 15/00; C12N 5/00; C12P 21/00; C07H 15/12
[52] U.S. Cl. .................... 435/172.3; 435/68; 435/240.4; 435/320; 536/27; 935/48; 935/56; 935/67
[58] Field of Search ............... 435/172.3, 240, 317, 435/240.4, 320, 68; 536/27

[56] References Cited

PUBLICATIONS

Izant et al., 1984, Cell 36: 1007–1015.
Chang et al., 1985, Mol. Cell. Biol. 5(9): 2341–2348.
Horsch et al., 1985, Science 228: 1229–1231.
Coleman et al., 1984, Cell 37: 429–436.
Watson, M., 1984, Nucl. Acids Res. 12(13): 5145–5164.
Broglie et al., 1984, Science 224: 838–843.
Grierson et al., 1985, Planta 163: 263–271.
Slater et al., 1985, Plant Mol. Biol. 5: 137–147.
Grierson et al., 1986, Phil. Trans. R. Sol. London B 314: 399–410.
Grierson et al., 1986, Nucl. Acids Res. 14(21): 8595–8603.

Primary Examiner—Charles F. Warren
Assistant Examiner—David T. Fox
Attorney, Agent, or Firm—Bertram I. Rowland

[57] ABSTRACT

Polygalacturonase DNA sequence and its use in modulating polygalacturonase expression in plant cells. DNA constructions are provided. The transit peptide finds use with heterologous peptides.

14 Claims, 1 Drawing Sheet

```
       10         20         30         40         50         60         70
GAATTCAATA GACAAGTTTA AAAACCATAC CATATAACAA TATATCATGG TTATCCAAAG GAATAGTATT
       80         90        100        110        120        130        140
CTCCTTCTCA TTATTATTTT TGCTTCATCA ATTTCAACTT GTAGAAGCAA TGTTATTGAT GACAATTTAT
      150        160        170        180        190        200        210
TCAAACAAGT TTATGATAAT ATTCTTGAAC AAGAATTTGC TCATGATTTT CAAGCTTATC TTTCTTATTT
      220        230        240        250        260        270        280
GAGCAAAAAT ATTGAAAGCA ACAATAATAT TGACAAGGTT GATAAAAATG GGATTAAAGT GATTAATGTA
      290        300        310        320        330        340        350
CTTAGCTTTG GAGCTAAGGG TGATGGAAAA ACATATGATA ATATTGCATT TGAGCAAGCA TGGAATGAAG
      360        370        380        390        400        410        420
CATGTTCATC TAGAACACCT GTTCAATTTG TGGTTCCTAA AAACAAGAAT TATCTTCTCA AGCAAATCAC
      430        440        450        460        470        480        490
CTTTTCAGGT CCATGCAGAT CTTCTATTTC AGTAAAGATT TTTGGATCCT TAGAAGCATC TAGTAAAATT
      500        510        520        530        540        550        560
TCAGACTACA AAGATAGAAG GCTTTGGATT GCTTTTGATA GTGTTCAAAA TTTAGTTGTT GGAGGAGGAG
      570        580        590        600        610        620        630
GAACTATCAA TGGCAATGGA CAAGTATGGG GGCCAAGTTC TTGCAAAATA AATAAATCAC TGCCATGCAG
      640        650        660        670        680        690        700
GGATGCACCA ACGGCCTTAA CCTTCTGGAA TTGCAAAAAT TTGAAAGTGA ATAATCTAAA GAGTAAAAAT
      710        720        730        740        750        760        770
GCACAACAAA TTCATATCAA ATTGAGTCA TGCACTAATG TTGTAGCTTC AAATTTGATG ATCAATGCTT
      780        790        800        810        820        830        840
CAGCAAAGAG CCCAAATACT GATGGAGTCC ATGTATCAAA TACTCAATAT ATTCAAATAT CTGATACTAT
      850        860        870        880        890        900        910
TATTGGAACA GGTGATGATT GTATTTCAAT TGTTTCTGGA TCTCAAAATG TGCAGGCCAC AAATATTACT
      920        930        940        950        960        970        980
TGTGGTCCAG GTCATGGTAT AAGTATTGGA AGCTTAGGAT CTGGAAATTC AGAAGCTTAT GTGTCTAATG
      990       1000       1010       1020       1030       1040       1050
TTACTGTAAA TGAAGCCAAA ATTATCGGTG CCGAAAATGG AGTTAGGATC AAGACTTGGC AGGGAGGATC
     1060       1070       1080       1090       1100       1110       1120
TGGACAAGCT AGCAACATCA AATTTCTGAA TGTGGAAATG CAAGACGTTA AGTATCCCAT AATTATAGAC
     1130       1140       1150       1160       1170       1180       1190
CAAAACTATT GTGATCGAGT TGAACCATGT ATACAACAGT TTTCAGCAGT TCAAGTGAAA AATGTGGTGT
     1200       1210       1220       1230       1240       1250       1260
ATGAGAATAT CAAGGGCACA AGTGCAACAA AGGTGGCCAT AAAATTTGAT TGCAGCACAA ACTTTCCATG
     1270       1280       1290       1300       1310       1320       1330
TGAAGGAATT ATAATGGAGA ATATAAATTT AGTAGGGGAA AGTGGAAAAC CATCAGAGGC TACGTGCAAA
     1340       1350       1360       1370       1380       1390       1400
AATGTCCATT TTAACAATGC TGAACATGTT ACACCACACT GCACTTCACT AGAAATTTCA GAGGATGAAG
     1410       1420       1430       1440       1450       1460       1470
CTCTTTTGTA TAATTATTAA TTTATACTAT AGATCTTGAA TATATAGCAG ATATGATATA TCACAATAAA
     1480       1490       1500       1510       1520       1530       1540
CAAATCTATA TCTATGTATT GAATAATTAT TATTAATATG TACGGATTGA AGTTTTAATA AGACTACTAT
     1550       1560       1570       1580       1590       1600       1610
GTATTTCTAT TTTCTAGTCA AAAGTTTGAC GATTGTACTT TTTAATGTAC AAAAATAATA AAATGGTTAT
     1620
TTATATGGGA ATTC
```

FIG. 1

PG GENE AND ITS USE IN PLANTS

CROSS-REFERENCE TO RELATED APPLICATIONS

This application is a continuation in part of Application Ser. No. 920,574 filed Oct. 17, 1986, which was a continuation in part of Application Ser. No. 845,676, filed Mar. 28, 1986, now abandoned, both of which are incorporated herein by reference.

FIELD OF THE INVENTION

The present invention relates to methods for isolating the plant polygalacturonase gene providing a transit peptide leader and modifying polygalacturonase production in plants.

BACKGROUND OF THE INVENTION

There has been substantial success in the production of proteins in mammalian cells and bacteria, which has been the primary focus and success of genetic engineering, while progress with the genetic engineering of plants has proven to be of substantially greater difficulty. With plants, one must usually modify the naturally occurring plant cell in a manner in which the cell can be used to generate a plant. Even in the event that this is successful, it is frequently essential that the modification be subject to regulation. That is, it will be of interest that the particular gene be regulated as to the differentiation of the cells and maturation of the plant tissue. There is also interest as to the site where the product is directed within the plant cell. Thus, there are substantially increased degrees of difficulty in genetically engineering plants.

Furthermore, plants have a larger number of chromosomes than the mammalian genome. Isolating specific genes and their regulatory regions in plants requires a major effort. Associated with this effort is the need to isolate DNA from a library, device techniques for demonstrating the presence of the gene on a particular fragment, isolating the gene from the fragment, providing that the gene is the correct gene, verifying that the product of the gene is the correct protein, and manipulating the gene so that it may be used for an intended purpose.

The path for genetic engineering of plants is a long and arduous one, further exacerbated by the need to go from cells to plants, which greatly extends the period of time before one can establish the utility of one's genetic construction. There is the further concern of the generality of the construction as to its use in different plant species. In addition, there is the necessary screening, where one wishes to localize the expresssion of the particular construction in particular cell types and the further concern that the genetically modified plant retain the genetic modification through a plurality of generations.

DESCRIPTION OF THE RELEVANT LITERATURE

Ali and Brady, *Aust. J. Plant Physiol* (1982) 9: 155–169 and Tucker and Grierson, *Planta* (1982) 155: 64–67 describe the PG2A form of the polygalacturonase enzyme. Grierson et al., *Planta* (1985) 163: 263–271 and Slater et al., *Plant Mol. Biol.* (1985) 5: 137–147 indicate the difficulty in recognizing PG mRNA by in vitro translation and immunopreciptiation. See also, Grierson et al., *Nucl. Acids Res.* (1986) 14: 3595–8603. The abundance of polygalacturonase (PG) mRNA during tomato fruit ripening is reported by DellaPenna et al., *Proc. Natl. Acad. Sci. USA* (1986) 83: 6420–6424.

SUMMARY OF THE INVENTION

Isolation of the polygalacturonase gene, its accompanying regulatory regions, and its use in the modulation of PG expression and as a source of the transit peptide for use with heterologous genes in DNA constructs is provided.

BRIEF DESCRIPTION OF THE DRAWING

FIG. 1 is the nucleotide sequence of PG's cDNA clone F1, with the underlined codons representing the start (47–49) and stop (1418–1420) of the open reading frame. The codon for the N-terminus of purified PG2A polypeptide is located at position 260–262 (GGG).

DESCRIPTION OF THE SPECIFIC EMBODIMENTS

Novel nucleic acid compositions and constructs are provided, including their use for controlling expression of polygalacturonase (PG) in plant cells or in combination with heterologous sequences controlling transport of peptides in plant cells to the cell wall.

In accordance with the subject invention, the cDNA coding for PG, the leader sequence for the PG precursor, expression constructs providing for transcription of PG in the sense of anti-sense direction, as well as expression of PG are provided. The constructs are introduced into plant cells from which plants may be regenerated, where the plants are modified as to amount of expression of PG, heterologous proteins are directed to the cell wall, and the DNA sequences may be used for isolating genomic DNA coding for PG, as well as the regulatory regions controlling the transcription of PG.

A sequence or fragment thereof is provided as depicted in FIG. 1. The sequence may be used in a variety of ways. Fragments of the sequence of at least about 10 bp, more usually at least about 15 bp, and up to and including the entire sequence may be employed as probes for detecting genomic DNA, for use in providing anti-sense sequences for inhibiting the expression of PG in plant cells, or for providing fusion proteins, where a portion of the PG gene is expressed in conjunction with another gene. Of particular interest for this purpose is the use of the transit peptide, which includes a fragment up to and including about 71 codons, usually including at least about the first 25 codons, more usually at least about the first 27 codons, and up to and including the first 71 codons, or any intermediate number of codons may be employed. In addition, an additional functional sequence involved with processing, maturation and protein utilization, e.g. translocation in the cell, involves the last 13 codons of the open reading frame immediately upstream from the stop codon and the oligopeptide encoded by this sequence. Codons may be replaced to provide for conservative substitutions, usually not more than 5, more usually not more than 3 non-conservative substitutions will be involved.

The transit peptide encoding sequence or functional fragment thereof may be used in conjunction with other than an opening reading frame coding for polygalacturonase (foreign gene) to provide for transfer of the foreign gene to the cell wall. The foreign gene may be endogenous or exogenous to the plant cell host. Conveniently, the transit peptide encoding sequence can be provided joined to the native transcriptional initiation region in proper orientation and joined at its 3'-terminus to a polylinker for insertion of the foreign gene in proper reading frame with the transit peptide encoding sequence. Alternatively, a convenient restriction site may be provided downstream from the processing site for insertion or an adapter may be prepared which joins the transit peptide encoding sequence at a site upstream from the processing site and joins the foreign gene at its 5'-terminus or internal to the foreign gene where the adapter includes the sequence coding for the processing site (site of maturation) and any additional nucleotides desired for the foreign gene.

The coding sequences may be used in their sense or anti-sense orientation. For the anti-sense orientation, see, for example, U.S. patent application Ser. No. 920,574. The anti-sense orientation allows for inhibiting the expression of PG. Thus, hydrolysis of poly(1,4-α-D-galacturonide)glycan (pectin) is inhibited.

For enhanced expression of PG, the PG cDNA gene may be inserted into an expression vector for exression in plants, either constituitively or inducible. Depending on the promoter which is employed, the continuous or regulated expression of PG may be achieved. A wide variety of promoters have been isolated, which are functional not only in the cellular source of the promoter, but also in numerous other plant species. There are also other promoters, e.g. viral and Ti-plasmid which can be used. These promoters include promoters from the Ti-plasmid, such as the octopine synthase promoter, the nopaline synthase promoter, the mannopine synthase promoter, promoters from other open reading frames in the T-DNA, such as ORF7, etc. Promoters which have been isolated and reported for plants include ribulose-1,3-biphosphate carboxylase small subunit promoter, phaseolin promoter, etc.

By appropriate manipulation of the promoter region and the subject cDNA gene, the cDNA gene may be joined to the promoter, so as to be subject to the transcriptional initiation regulation of such promoter. In addition, the transcriptional termination region can be provided downstream from the structural gene to provide for efficient termination. The termination region may be obtained from the same genes as for the promoters or may be obtained from different genes, the choice of termination region being primarily one of convenience.

The promoter region will be within about 100 bp of the first base of the mRNA, more usually within about 50 bp of the first base. The termination region will usually be within about 200 bp of the last base of the structural gene, more usually within about 100 bp of the last base of the structural gene.

Depending upon the manner in which the expression cassette comprising the promoter region structural gene and termination region are to be integrated into the plant cell genome, additional DNA sequences may be involved. Where the Ti- or Ri-plasmid are employed, the expression cassette will normally be joined to at least the right border of T-DNA, and usually both borders of T-DNA. The T-DNA expression cassette construct will then be introduced into a Ti- or Ri-plasmid, conveniently by conjugation and homologous recombination. This technique has been extensively described in the literature, see, for example, Comai et al., *Plasmid* (1983) 10: 21–30, PCT Publication Nos. WO84/02913, 02919, 02920 and EPO Publication 0 116 418. Alternatively, binary vectors may be employed, where the Ti- or Ri-plasmid of the Agrobacterium may or may not have aT-region homologous with the T-DNA of the construct. In either event, so long as the vir genes are present on an endogenous plasmid, the T-DNA can be transferred successfully to the plant.

The expression construct will normally be joined to any other sequences of interest, such as the T-DNA sequences, in conjunction with prokaryotic or vector DNA for cloning in a bacterial host. These vectors may then be used directly for introduction into the plant genome by such techniques as (1) electroporation, (2) cocultivation, (3) microinjection, or the like. These techniques have been described in the literature, see, for example: (1) Fromm et al. *PNAS* (1985) 82: 5824–5828; (2) Horsch et al. *Science* (1985) 228: 1229–1231, Herrera-Estrella et al. *Nature* (1983) 303: 209–313; and (3) Crossway et al. *Biotechniques* (1986) 4: 320–334, Lin, *Science* (1966) 151: 333–337, and Steinkiss and Stabel, *Protoplasma* (1983) 116: 222–227.

A large number of vectors are available for replication in bacterial hosts. A number of these vectors are commercially available, such as λgt10 and 11, the pUC series, M13 series, pBR322, pACYC184, or the like. The selection of vector will be dependent upon preparative convenience, availability, copy number, size, and the like.

At each state, the various fragments may be manipulated by endonuclease restriction, in vitro mutagenesis, primer repair, resection, e.g. Bal31, tailing with TdT, ligation with linkers or adapters, or the like. Mutagenesis may be employed for deletions, insertions, removing or introducing a convenient restriction site, or the like. The steps are amply described in the literature, and need not be expanded upon here.

Once the construct is formed, it may be introduced into the plant cell in accordance with conventional ways as described above. Usually, the expression cassette will be joined to a marker which allows for selection of the expression cassette in the plant cell. Various markers exist which find use in plant cells, particularly markers which provide for antibiotic resistance. These markers include resistance to G418, hygromycin, bleomycin, kanamycin and gentamicin. These genes will normally be under the transcriptional initiation control of constituitive promoters, such as some of the promoters described previously. After transforming the cells, those cells having the construct will be selected by growing in a selected medium, ultimately providing for the production of callus, where cell suspensions have been used during the transformation. Shoots may then be isolated from the callus and grown in appropriate medium to produce plants. Alternatively, explants such as leaf disc or embryos may be transformed, selected by growing in a selective medium. Regenerated shoots may then be isolated and grown in appropriate medium to produce plants.

The subject constructs may be used with a wide variety of plants, particularly fruit bearing plants, such as tomatoes, strawberries, avocados, tropical fruits such as papayas, mangos, etc., and pome fruits such as pears, apples, peaches, nectarines and apricots. The resulting plants will then be modified in the amount of PG that is produced, particularly during the ripening cycle. Alternatively, heterologous genes may be employed which may be transported to the cell wall. Genes of interest for transport to the cell wall include carbohydrate metabolizing enzymes, such as invertase, dextransucrase, levansucrase; proteins involved in disease resistance such as chitinase, hydroxyproline-rich glycoproteins, fungal and bacterial PG-inhibiting proteins; and cell wall metabolizing enzymes.

The PG gene may be obtained by initially employing a DNA library prepared in accordance with conventional conditions from mRNA prepared from ripe tomato fruit. The library may then be screened employing PG-specific probes, which may be prepared in accordance with the amino acid sequence of PG. In addition, antibodies may be prepared which may be used for detection of expression of PG. Clones which hybridize with the probe are then isolated, the fragments restricted, and the smaller fragments sequenced for detection of coding regions for PG. Those clones having the cDNA sequence coding for PG are isolated, the fragment coding for the PG gene excised and further manipulated as described previously.

The following examples are offered by illustration and not by way of limitation.

EXPERIMENTAL

Bacterial Strains

TABLE I

| Bacterial Strains | | |
|---|---|---|
| *Escherichia Coli* Designation | Phenotype | Origin/Reference |
| 7118 | Δlac | Vieira and Messing Gene (1982) 19:259–268 |
| Y1088 | hsdR$^-$ hsdM$^+$ | Young and Davis |
| Y1090 | Δlon | PNAS USA (1983) 80:1194–1198 |
| C2110 | polA | Stalker et al. PNAS USA (1983) 80:5500–5504 |
| C600 | F—, λ- | Maniatis et al., Molecular Cloning, A Laboratory Manual, Cold Spring Harbor, New York, 1982 |
| C600 (hfr) | hfr 150 | Young and Davis, supra. |

Enzymes and Radioisotopes

All enzymes were obtained from commercial sources and used according to the manufacturer's suggestions. Radioisotopes were obtained from New England Nuclear.

Isolation of poly(A)+RNA

Ripe fruit of tomato cv. CaliGrande was harvested and frozen in liquid $N_2$. Frozen tissue was ground in a mortar and pestle in liquid $N_2$, and the resulting powder was extracted by homogenization with a Brinkman polytron in buffer described by Facciotti et al. *Bio-/Technology* (1985) 3: 241–246. Total RNA was prepared as described by Colbert et al. *Proc. Natl. Acad. Sci. USA* (1983) 80: 2248–2252.

Polysaccharides were precipitated from total RNA preparations with 40 mM sodium acetate and 0.5 vol ethanol (Mansson et al. *Mol. Gen. Genet.* (1985) 200: 356–361. Poly(A)+RNA was isolated as described by Maniatis et al. (1982) supra.

Synthesis of cDNA

Synthesis of cDNA from poly(A)+RNA was performed as described by Gubler and Hoffman, *Gene* (1983) 25: 263–269 with the following modifications: The reaction mixture for synthesis of the first strand included 1 mM dGTP, 1 mM dATP, 1 mM TTP, 0.5 mM dCTP, 0.5 unit/μl RNasin (Promega), 4 μg of tomato poly(A)+RNA, and 80–100 units of reverse transcriptase (Life Sciences). The reaction was stopped with 2 μl of 500 mM EDTA, then precipitated with 10 μg tRNA, 1 vol 4M $NH_4OAc$, and 2.5 vol of ethanol overnight on dry ice.

Second strand synthesis was performed from approximately 500 ng of the first strand reaction product. Aliquots of the first and second strand reaction mixtures were radiolabeled separately with 20 μCi of 5'-[α-$^{32}$P] dCTP to monitor each reaction independently.

Cloning of Double-Stranded cDNA in λgt11 and λgt10.

The double-stranded cDNA was EcoRI methylated as described by the manufacturer (New England Biolabs). After ethanol precipitation, the cDNA ends were blunted using 3 units of the Klenow fragment of DNA polymerase I (Bethesda Research Laboratories); the following conditions: 66 mM Tris-HCl pH 7.5, 20 mm $MgCl_2$, 100 μM dithiothreitol, 100 μM each of dGTP, dATP, TTP, and dCTP at room temperature for 1 hr. The DNA was then ethanol precipitated. After blunting, 2 μg of EcoRI phosphorylated linkers were added to the cDNA in 10 μl of ligase buffer (50 mM Tris, pH 7.5, 10 mM $MgCl_2$, 20 mM dithiothreitol, 1 mM ATP, and 5 mg/ml bovine serum albumin). T4 DNA ligase (1 Weiss unit, *Weiss*, J. Biochem. (1968) 243: 4543, Promega) was added and incubated for 6 hr at 15° C. An additional Weiss unit of T4 DNA ligase in 10 μl of ligase buffer was then added and incubated for 24 hr at 15°–19° C. The reaction was phenol extracted, ethanol precipitated and digested within 100 units EcoRI (New England Biolabs) for 6–8 hrs, phenol extracted and ethanol precipitated. Excess linkers and cDNA fewer than 500 base pairs were removed by chromatography on Bio-gel A-50 m (100–200 mesh) and the sized cDNA was ligated to EcoRI-cleaved λgt11 and λgt10 vector DNA (Statagene) as described by Huynh et al. in DNA Cloning: A Practical Approach, ed. D. M. Glover, pp. 49–78, IRL Press, Oxford, England, 1985.

In vitro packaging reactions were performed with Giga-pack extracts (Stratagene) as described by the vendor. Initial test ligations and in vitro packaging were done using various dilutions of cDNA to empirically determine the optimal ratio of cDNA/vector for production of recombinant phage. The packaged λgt11 phage were plated on *E. Coli* Y1088 in the presence of isopropyl-1-thio-β-D-galactoside (IPTG) and 5-bromo-4-cloro-3-indolyl-β-D-galactoside (X-gal) as described by Huynh et al. (1985), supra to determine the number of recombinants. Greater than $5 \times 10^6$ recombinants at a 90% insertion rate was obtained in λgt11. Packaged λgt10 phage were plated on *E. coli* C600 (hfr) and a similar number of recombinants and insertion rate were obtained.

Library Screening

Approximately 200,000 phage from an unamplified λgt11 library were screened at a density of 20,000 plaque-forming units per 9 cm square plate using *E. coli* Y1090 as the host as described by Huynh et al. (1985), supra, except that NZY media (per liter: 5 g NaCl, 2 g $MgCl_2$, 10 g NZamine type A (Sheffield Products), 5 g yeast extract and 15 g agar) was used. Plates were incubated and overlaid with nitrocellulose sheets containing IPTG as described by Huynh et al. (1985), supra. The nitrocellulose sheets were saturated with 0.5M Tris pH 8.0, 0.15M NaCl, 0.02% $NaN_3$, 0.1% Triton X-100 and 5% non-fat dry milk, then incubated 30 min at room temperature with the same buffer containing antipolygalacturonase antibody (see below) diluted 1:1000. Bound antibody was detected with an alkaline phosphatase-conjugated second antibody (Promega) as described by the vendor. Positive plaques were purified by successive plating and phage DNA was prepared as described (Maniatis et al. (1982), supra).

The λgt10 library was plated at a density of 10,000 plaque-forming units per 22 cm$^2$ plate. Approximately 20,000 phage were screened with a $^{32}$P-labeled PG-specific probe as described by Huynh et al., supra. The probe was derived from a PG cDNA clone identified in the λgt11 library screen. Positive plaques were purified by successive plating and phage DNA was prepared as described by Maniatis et al., supra.

Subcloning and Sequencing of cDNA Insert P1 and F1

Phage DNA from positive plaques designated P1 and F1 were digested with EcoRI and the resulting fragments were subcloned in EcoRI-digested vector M13 Blue Scribe Minus (Stratagene) by in vitro ligation. Initial DNA sequencing was performed using single-stranded template from the Blue Scribe construct prepared as described by the manufacturer. All DNA sequencing was performed as described by Sanger et al., *Proc. Natl. Acad. Sci. USA* (1977) 74: 5463 or Maxam and Gilbert, *Methods Enzymol.* (1980) 64: 499-580. Overlapping sequences were obtained by subcloning purified BamHI-EcoRI, HindIII-EcoRI, and BamHI-HindIII fragments (Maniatis et al., supra) from the Blue Scribe construct into M13 mp18 (Yanisch-Perron et al. *Gene* (1985) 53: 103-119) and M13 mp19 (Norrander et al. *Gene* (1983) 26: 101-106).

Additional sequencing was performed on sequential deletions produced from inserts cloned in both orientations into Bluescribe Minus. Deletions resulted from the use of exonuclease III and mung bean nuclease (Stratagene) as described by the vendor. Resulting fragments were subcloned into M13 vectors for sequencing.

Polygalacturonase Purification for Protein Sequencing

Total cell wall bound proteins were prepared from ripe fruit of cv. CaliGrande as described by *Crookes and Grierson, Plant Physiol.* (1983) 72: 1088-1093. The extract was dialyzed against 0.025M ethanolamine, pH 9.4, and applied to a 9×300 mm column of chromatofocusing exchanger PBE 94 (Pharmacia) equilibrated with 0.025M ethanolamine, pH 9.4. Bound proteins were eluted with Polybuffer 96, pH 8.0 (Pharmacia). Fractions containing polygalacturonase were pooled and precipitated with ammonium sulphate (90% saturation) and further fractionated by chromatography over a hydroxyapatite (HAPT) HPLC column. Two ml volumes were layered onto the column and chromatographed at 1 ml/min using a linear gradient extending from 10 mM to 350 mM sodium phosphate, pH 6.8. Samples were monitored at A$_{280}$ and fractionated into 0.5 ml volumes. Fractions collected from numerous runs which contained polygalacturonase were pooled and dialyzed against 6% acetic acid, then lyophilized.

Protein Sequencing

Polygalacturonase prepared as described above was sequenced intact with a Beckman 890M Liquid Phase Amino Acid Sequencer. The following N-terminal sequence was obtained:

gly-ile-lys-val-ile-asn.

Polygalacturonase Purification for Antibody Production

Tomato cell wall bound proteins were prepared from ripe fruit of cv. UC82B as described by Tucker and Grierson, *Planta* (1982) 155: 64-67. The pellet from ammonium sulphate precipitation was dissolved in 150 mM NaCl and then dialyzed overnight against the same buffer.

The protein solution was then fractionated on a TSK 3000/2000 HPLC sizing column using an isocratic gradient containing 10 mM NaCl and 10 mM Tris pH 7.2 at a flow rate of 0.5 ml/min.

TSK fractions containing polygalacturonase activity (Reisfeld et al. *Nature* (1962) 195: 281-283) were pooled and and further fractionated over an hydroxyapatite HPLC column using a linear gradient of 10 mM-350 mM sodium phosphate, pH 6.8, and a flow rate of 1 ml/min. The peak containing polygalacturonase activity was collected and used to inject rabbits for antibody production.

Polygalacturonase for booster injections was prepared by resolving the cell wall bound protein preparation on SDS polyacrylamide gels. The material precipitated with ammonium sulphate (see above) was electrophoresed on 3 mm thick and 14 mm wide gels containing 12.5% polyacrylamide (Laemmli, *Nature* (1970) 227: 680-685) and proteins were visualized by staining with Coomassie Brilliant Blue R. The region corresponding to the polygalacturonase bands (approximately 40,000-43,000 daltons) was excised, frozen, and ground with liquid N$_2$.

Antibody Preparation

One rabbit was given 4 injections of polygalacturonase (125 μg injection) over a one month period. The same rabbit was then given a booster injection of polygalacturonase (approximately 150 μg) recovered from SDS polyacrylamide gels. An identical booster injection was again given one week after the first. The animal was exsanguinated 2 weeks later as a source of serum.

Six ml of the crude serum were diluted with 6 ml of 0.1M sodium phosphate, pH 7.0, and applied to a 6 ml column of Protein A-Sepharose (Sigma). The column was washed with 80 ml of 0.1M sodium phosphate, pH 7.0, and the IgG fraction was then eluted with 0.1M glycine, pH 3.0. Fractions with the highest A$_{280}$ were pooled, dialyzed against 20 mM sodium phosphate pH 7.6, 150 mM NaCl and concentrated on an Amicon XM80 membrane. Glycerol was then added to a final concentration of 40%.

Affinity purified antiserum was prepared by incubating the IgG fraction with polygalacturonase linked to a Tresacryl (Pharamacia) affinity chromatography matrix as described by the vendor. Polygalacturonase purified for protein sequencing was linked to 4 ml of Tresacryl resin as described by the manufacturer. Five ml of IgG prepared as described above was diluted with 50 ml with 0.01M Tris pH 7.5, 150 mM NaCl and 0.1% Tween-20 (TBST) and incubated with the resin overnight at 4° C. The resin was then washed with TBST and eluted with 0.2M glycine, pH 2.75. Fractions with A$_{280}$ absorption were pooled and dialyzed against 10 mM Tris pH 8.0, 150 mM NaCl. The final volume of purified antibody was 12 ml representing a 1:2 dilution of the original serum.

DNA Probe Preparation

DNA was digested with EcoRI and sized by electrophoresis on agarose gels. DNA fragments for use as $^{32}$P-labeled probes in DNA blot hybridization experiments were excised from low melt agarose melted at 65° C. for 30 min. and purified by phenol extraction, chromatography on Elutip-d Columns (Schleicher & Schuel) and ethanol precipitation. DNA was $^{32}$P- labeled by nick translation (Bethesda Research Laboratories) as described by the vendor.

RESULTS

Identification of Polygalacturonase cDNAs

Twelve putative polygalacturonase clones were identified from the λgt11 library by reaction with the antibody preparation described above. Using inserts purified from two of the clones as probes, Northern analysis demonstrated that one clone (C3) encoded mRNA expressed during tomato development in the manner and size expected for polygalacturonase mRNA.

To identify additional putative cDNA clones encoding polygalacturonase, phage DNA was prepared from the remaining 10 clones, digested with EcoRI and HindIII, and subjected to Southern blot hybridization analysis (Maniatis et al., supra) using clone C3 insert as a probe. An additional cDNA clone (P1) cross-hybridized to C3 and was further characterized to provide sequences for anti-sense expression. The identity of P1 as a polygalacturonase cDNA clone was confirmed by comparison of the amino acid sequence predicted from the DNA sequence to the actual polygalacturonase protein sequence. The clone encodes a portion of the polygalacturonase gene beginning approximately at the N-terminus of the mature polygalacturonase polypeptide and extending to the carboxy terminus including the 3' untranslated region.

The 5'BamHI-EcoRI fragment of P1 was used as a probe to screen the λgt10 library. Positive signals for 31 plaques resulted from a screen of 20,000 clones. Phage DNA prepared from ten of the clones was digested with BamHI and EcoRI, and subjected to Southern blot analysis using the 5'BamHi-EcoRI fragment of P1 as a probe. Eight of the ten clones contained a BamHI-EcoRI fragment approximately 300 bp larger than the 5'BamHI-EcoRI fragment of P1. Clone F1 (1.6 Kb) is representative of this group.

The sequence of F1 is detailed in FIG. 1. Identification of the translation start and stop codons gives an open reading frame from base position 47 to position 1417, encoding a polypeptide of 50,075 Da.

The amino-terminus of PG2A corresponds to the codon GGG at base positions 260–262. The remaining open reading frame encodes a polypeptide of 386 amino acids (Mr 40,279) before the C-terminal serine of PG2A. Thus, two functional maturation peptides, e.g. transit peptides are defined at the N- and C-terminus of the protein.

The F1 EcoRI fragment was inserted into Bluescribe (Stratagene) creating pCGN1404 in one orientation and pCGN1408 in the reverse orientation.

pCGN1404 was cut with EcoRI and the purified EcoRI insert ligated into the EcoRI site of pCGN46 (Comai et al., *Nature* (1985) 317: 741–744) creating pCGN1406 which is a Mas 5' PG full length sense Ocs 3' cassette. The Mas PG anti-sense Ocs cassette pCGN1409 was created by cutting pCG1406 with EcoRI, ligation and selection of the anti-sense orientation.

pCGN1406 and pCGN1409 were cut with Xho1 and ligated into Sall digested pCGN783 creating pCGN1411 PG anti-sense and pCGN1412 PG sense binaries (plasmids for conjugation with *A. tumefaciens*. Construction of pCGN783

Construction of pCGN167

To construct pCGN167, the AluI fragment of CaMV (bp 7144–7735) (Gardner et al. *Nucl. Acids Res.* (1981) 9: 2871–2888) was obtained by digestion with AluI and cloned into the HincII site of M13 mp7 (Vieira *Gene* (1982) 19: 259) to create C614. An EcoRI digest of C614 produced the EcoRI fragment from C614 containing the 35S promoter which was cloned into the EcoRI site of PUC8 (Vierra et al., *Gene* (1982) 19: 259) to produce pCGN146.

To trim the promoter region, the BglII site (bp 7670) was treated with BglII and Bal31 and subsequently a BglII linker was attached to the Bal31 treated DNA to produce pCGN147.

pCGN148a containing a promoter region, selectable marker (KAN with 2 ATG's) and 3' region was prepared by digesting pCGN528 (see below) with BglII and inserting the BamHI-BglII promoter fragment from pCGN147. This fragment was cloned into the BglII site of pCGN528 so that the BglII site was proximal to the kanamycin gene of pCGN528.

The shuttle vector used for this construct, pCGN528, was made as follows. pCGN525 was made by digesting a plasmid containing Tn5 which harbors a kanamycin gene (Jorgenson et al. *Mol. Gen.* (1979) 177: 65) with HindIII-BamHI and inserting the HindIII-BamHI fragment containing the kanamycin gene into the HindIII-BamHI sites in the tetracycline gene of pACYC184 (Chang & Cohen *J. Bacteriol.* (1978) 134: 1141–1156). pCGN526 was made by inserting the BamHI fragment 19 of pTiA6 (Thomashow et al. *Cell* (1980) 19: 729–739) into the BamHI site of pCGN525. pCGN528 was obtained by deleting the small XhoI fragment from pCGN526 by digesting with XhoI and religating.

pCGN149a was made by cloning the BamHI kanamycin gene fragment from pMB9KanXXI into the BamHI site of pCGN148a.

pMB9KanXXI is a pUC4K varient (Vieira & Messing, *Gene* (1982) 19: 259: 268) which has the XhoI site missing but contains a functional kanamycin gene from Tn903 to allow for efficient selection in Agrobacterium.

pCGN149a was digested with BglII and SpHI. This small BglII-SphI fragment of pCGN149a was replaced with the BamHI-SpHI fragment from M1 (see below) isolated by digestion with BamHI and SphI. This produces pCGN167, a construct containing a full length CaMV promoter, 1ATG-kanamycin gene, 3' end and the bacterial Tn903-type kanamycin gene. M1 is an EcoRI fragment from pCGN550 (see construction of pCGN587) and was cloned into the EcoRI cloning site of M13mp9 in such a way that the PstI site in the 1ATG-kanamycin gene was proximal to the polylinker region of M13mp9.

Construction of 709 (1ATG-Kanamycin-3' region)

pCGN566 contains the EcoRI-HindIII linker of pUC18 (Yanisch-Perron, ibid) inserted into the EcoRI-HindIII sites of pUC13-cm (K. Buckley, Ph.D. thesis, UC-San Diego, 1985). The HindIII-BglII fragment of pNW31c-8, 29-1 (Thomashow et al. (1980) *Cell* 19: 729) containing ORF1 and 2 (Barker et al. (1983), supra) was subcloned into the HindIII-BamHI sites of pCGN566 producing pCGN703.

The Sau3A fragment of pCGN703 containing the 3' region of transcript 7 from pTiA6 (corresponding to bases 2396–2920 of pTi15955 (Barker et al. (1983), supra) was subcloned into the BamHI site of pUC18 (Yanisch-Perron et al. (1985), supra) producing pCGN709.

Construction of pCGN766c (35s promoter—3' region)

The HindIII-BamHI fragment of pCGN167 (for construction see infra) containing the CaMV-35S promoter, 1ATG-kanamycin gene and the BamHI fragment 19 of pTiA6 was cloned into the BamHI-HindIII sites of pUC19 (Norrander et al. (1983), supra; Yanisch-Perron et al. (1985), supra) creating pCGN976.

The 35S promoter and 3' region from transcript 7 was developed by inserting a 0.7 kb HindIII-EcoRI fragment of pCGN976 (35S promoter) and the 0.5 kg EcoRI-SalI fragment of pCGN709 (transcript 7: 3', for construction, see supra) into the HindIII-SalI sites of pCGN566 creating pCGN766c.

Final Construction of pCGN783

The 0.7 kb HindIII-EcoRI fragment of pCGN766c (CaMV-35S promoter) was ligated to the 1.5 kb EcoRI-SalI fragment of pCGN726c (1-ATG-KAN-3' region) into the HindIII-SalI sites of pUC119 (J. Vieira, Rutgers University, N.J.) to produce pCGN778.

The 2.2 kb region of pCGN778, HindIII-SalI fragment containing the CaMV 35S promoter (1-ATG-KAN-3' region) replaced the HindIII-SalI polylinker region of pCGN739 to produce pCGN783.

These binaries are capable of transcription in plant cells under the Mas promoter. In the case of sense constructs polygalacturonase mRNA can be translated into protein. In the anti-sense construct transcribed mRNA will hybridize with endogenous sense PG mRNA and modulate the amount of free mRNA capable of translation, hence providing regulation of gene expression using anti-sense mRNA.

As is evident from the above results, the entire PG gene has been made available. Thus, the DNA sequences may be used in a variety of ways, as probes for isolation of the genomic gene and identification of the regulatory regions associated with the PG gene, as a source of sequences for modulating the production of PG, either enhancing the production of PG, by introducing the gene into a plant host, either constituitive production or inducible production, by providing for anti-sense sequences, either under constituitive or inducible transcription, where the production of PG may be reduced, as well as providing for fragment sequences, such as the transit peptide sequence for joining to heterologous genes for directing various peptides to the plant cell wall.

All references indicated herein are to be incorporated by reference as fully as if set forth verbatim.

Although the foregoing invention has been described in some detail by way of illustration and example for purposes of clarity of understanding, it will be obvious that certain changes and modifications may be practiced within the scope of the appended claims.

What is claimed is:

1. A DNA sequence which is uninterrupted, encodes tomato polygalacturonase (PG) and is flanked by at least one non-wild type DNA sequence 5' to or 3' to said polygalacturonase encoding sequence.

2. A DNA sequence according to claim 1, wherein said sequence is a cDNA sequence.

3. A DNA sequence according to claim 2, wherein said cDNA sequence encodes the tomato fruit PG2A isoform of polygalacturonase.

4. A DNA sequence according to claim 1, joined to a prokaryotic replication system.

5. A DNA sequence according to claim 4, comprising a marker for selection of a eukaryotic cell comprising said DNA sequence.

6. A cDNA encoding for tomato polygalacturonase.

7. A cDNA according to claim 6, wherein said polygalacturonase is tomato fruit PG2A isoform.

8. A DNA construct comprising a DNA sequence of at least 15 base pairs of a DNA sequence encoding tomato polygalacturonase (PG) joined, in the opposite orientation for expression, 5' to the 3' terminus of a transcriptional initiation region functional in plants.

9. A DNA construct according to claim 8, wherein said tomato polygalacturonase is the tomato fruit PG2A isoform.

10. A DNA construct according to claim 8, joined to a sequence encoding a marker capable of selection in a plant cell comprising said DNA construct.

11. A DNA construct according to claim 8, wherein said DNA sequence comprises a strand complementary to at least 200 and not greater than about 1420 nt of the messenger RNA of polygalacturonase.

12. A DNA construct comprising a transcriptional initiation region functional in plants joined at its 3' terminus to the 5' terminus of a tomato polygalacturonase transit peptide encoding sequence, said transit peptide encoding sequence joined to other than a sequence encoding mature tomato polygalacturonase.

13. A DNA construct comprising a transcription initiation region functional in a plant joined directly or through an intervening sequence to the 5' terminus of at least one of (a) at least 15 and no more than 259 nt of the 5'-terminal coding region of tomato polygalacturonase and (b) at least 39 nt of the 3'-terminal coding region of tomato polygalacturonase.

14. A tomato plant cell comprising a DNA construct according to any of claims 8 to 13.

* * * * *

UNITED STATES PATENT AND TRADEMARK OFFICE
CERTIFICATE OF CORRECTION

PATENT NO. : 4,801,540

DATED : January 31, 1989

INVENTOR(S) : William R. Hiatt; Raymond E. Sheehy; Christine K. Shewmaker; Jean C. Kridl; Vic Knauf It is certified that error appears in the above-identified patent and that said Letters Patent is hereby corrected as shown below:

In the specification, column 1, line 39, "device" should read --devise--; line 67, "immunopreciptiation" should read --immunoprecipitation--. Column 2, line 29, "of" should read --or--; line 64, "opening" should read --open--. Column 3, line 21, "exression" should read --expression--; line 22, "constituitively" should read --constitutive--; line 55, replace "region structural" with --region, structural--; line 58, "are" should read --is--. Column 4, line 2, "aT-region" should read --a T-region--; line 18, "Steinkiss" should read --Steinbiss--; line 45, "constituitive" should read --constitutive--. Column 6, line 15, "mm" should read --mM--; line 27, "within" should read --with--; line 33, "Statagene" should read --Stratagene--; line 43, "Coli" should read --coli--; line 45, "cloro" should read --chloro--; line 49, "phase" should read --phage--; line 57, "media" should read --medium--; line 63, "NaN3" should read --NaNO3--. Column 7, lines 17, 19, 26-27, "Blue Scribe", each occurrence, should read --Bluescribe--; line 28, "53" should read --33--. Column 8, line 9, delete second "and"; line 41, replace "phosphate pH" with --phosphate, pH--; line 66, "C." should read --C--. Column 9, line 33, "BamHi" should read --BamHI--; line 57, "pCG1406" should read --pCGN1406--. Column 10, lines 39 and 41, "SpHI", each occurrence, should read --SphI--. Column 10, lines 44, 51 and column 11, line 1, "1ATG", each occurrence, should read --1 ATG--. Column 11, lines 36 and 38, "constituitive", each occurrence, should read --constitutive--. Column 7, line 23, "64" should read --65--. Col. 10, line 49, "1ATG" should read --1 ATG--.

Signed and Sealed this

Eighth Day of January, 1991

Attest:

HARRY F. MANBECK, JR.

*Attesting Officer*   Commissioner of Patents and Trademarks